US012193837B2

(12) United States Patent
Brattain

(10) Patent No.: US 12,193,837 B2
(45) Date of Patent: *Jan. 14, 2025

(54) SYSTEM AND METHOD FOR ASSESSING ANIMALS CONSIDERING AUSCULTATION AND EVALUATION OF PHYSIOLOGICAL RESPONSES IN VARIOUS ENVIRONMENTS

(71) Applicant: INTERVET INC., Madison, NJ (US)

(72) Inventor: Kurt Brattain, Chaska, MN (US)

(73) Assignee: INTERVET INC., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/147,564

(22) Filed: Dec. 28, 2022

(65) Prior Publication Data
US 2023/0165525 A1 Jun. 1, 2023

Related U.S. Application Data

(63) Continuation of application No. 16/752,278, filed on Jan. 24, 2020, now Pat. No. 11,642,079, which is a
(Continued)

(51) Int. Cl.
A61B 5/0205 (2006.01)
A61B 5/00 (2006.01)
(Continued)

(52) U.S. Cl.
CPC .......... *A61B 5/4884* (2013.01); *A61B 5/0205* (2013.01); *A61B 5/7275* (2013.01);
(Continued)

(58) Field of Classification Search
CPC ... A61B 2503/40; A61B 5/0205; A61B 5/024; A61B 5/0816; A61B 5/4884; A61B 5/7275; A61B 7/003; A61B 7/02
See application file for complete search history.

(56) References Cited

U.S. PATENT DOCUMENTS 6,287,254 B1  9/2001  Dodds
7,376,457 B2  5/2008  Ross
(Continued)

FOREIGN PATENT DOCUMENTS

EP   3136962 B1    10/2020
WO   2008041130 A2  4/2008
(Continued)

OTHER PUBLICATIONS

European Substantive Examination Report in Application No. 20194875.9 dated Jul. 17, 2023, 5 pages.
(Continued)

Primary Examiner — Eric J Messersmith
(74) Attorney, Agent, or Firm — Berg Hill Greenleaf Ruscitti LLP

(57) ABSTRACT

The invention includes a system and method for predicting the performance of production animals by analysis of heart and lung sounds to determine likelihoods the animals will develop BRD or other diseases or ailments. Vital signs of animals are recorded during an adrenergic sympathetic "flight or fight" situation. A cardio-pulmonary rate ratio is determined for each animal by dividing a normalized adjusted heart rate value by a normalized adjusted respiratory value. From the ratios calculated for each animal in a group, a ratio range is established. Ratio values at a lower end of the ratio range indicate higher relative respiration rates and poor lung performance due to disease. Ratio values at an upper end of the range may indicate low cardiac output and an inability to tolerate rapid weight gain. Ratio values at either end of the range may indicate compromised cardio-pulmonary function.

14 Claims, 6 Drawing Sheets

Related U.S. Application Data continuation of application No. 15/307,141, filed as application No. PCT/US2015/028373 on Apr. 29, 2015, now Pat. No. 10,575,776.

(60) Provisional application No. 61/985,935, filed on Apr. 29, 2014.

(51) Int. Cl.
    *A61B 7/00*     (2006.01)
    *A61B 7/02*     (2006.01)
    *A61B 5/024*     (2006.01)
    *A61B 5/08*     (2006.01)

(52) U.S. Cl.
    CPC ............... *A61B 7/003* (2013.01); *A61B 7/02* (2013.01); *A61B 5/024* (2013.01); *A61B 5/0816* (2013.01); *A61B 2503/40* (2013.01)

(56) References Cited

U.S. PATENT DOCUMENTS

| | | |
|---|---|---|
| 2002/0010390 A1 | 1/2002 | Guice et al. |
| 2005/0137487 A1 | 6/2005 | Zhu et al. |
| 2006/0020295 A1 | 1/2006 | Brockway et al. |
| 2007/0173704 A1* | 7/2007 | Bjorno ................. G16H 50/30 600/300 |
| 2010/0145167 A1* | 6/2010 | Im ........................ A61F 5/56 600/301 |
| 2012/0197323 A1 | 8/2012 | Elferri et al. |
| 2012/0215077 A1 | 8/2012 | Geissler et al. |
| 2013/0338497 A1 | 12/2013 | Tupin, Jr. |

FOREIGN PATENT DOCUMENTS

| | | |
|---|---|---|
| WO | 2008130549 A1 | 10/2008 |
| WO | 2015168341 A1 | 11/2015 |

OTHER PUBLICATIONS

New Zealand Patent Examination Report 1 in Application No. 725766, dated Mar. 18, 2021, 7 pages.
European Search Report in Application No. 20194875.9-1115, dated Dec. 9, 2020, 8 pages.
Australian Patent Examination Report 1 in Application No. 2020200859, dated Jun. 19, 2020, 4 pages.
International Search Report and Written Opinion for International (PCT) Patent Application No. PCT/US2015/028373, mailed Aug. 31, 2015, 9 pages.
Office Action dated Sep. 11, 2017 in European Patent Application No. 15786150.1.
Examination Report dated Feb. 8, 2019 in Australian Patent Application No. 2015253094.
European Substantive Examination Report in EP Application No. 20194875.9 dated Mar. 22, 2024, 4 pages.

* cited by examiner

SYSTEM AND METHOD FOR ASSESSING ANIMALS CONSIDERING AUSCULTATION AND EVALUATION OF PHYSIOLOGICAL RESPONSES IN VARIOUS ENVIRONMENTS

CROSS REFERENCE TO RELATED APPLICATIONS

This application is a continuation of U.S. application Ser. No. 16/752,278, filed Jan. 24, 2020, which is a continuation of U.S. application Ser. No. 15/307,141, filed Oct. 27, 2016, now U.S. Pat. No. 10,575,776, which is a national stage application under 35 U.S.C. 371 of PCT Application No. PCT/US2015/028373, filed on Apr. 29, 2015, which designated the United States, which PCT application claims priority under 35 U.S.C. § 119(e) to U.S. Provisional Patent Application Ser. No. 61/985,935 filed Apr. 29, 2014, each of which are incorporated herein in their entireties by reference.

FIELD OF THE INVENTION

The present invention generally relates to non-invasive evaluations of animals for indications of tolerance to stress or history of disease or trauma as measured by cardio-pulmonary function. More particularly, to a system and method for predicting: the performance of production animals, the capacity of activities for all animals, and the likelihood of morbidity and mortality by analysis of thoracic heart and lung sounds.

BACKGROUND OF THE INVENTION

Cardiovascular diseases, respiratory diseases, and gastrointestinal diseases have been distinguished according to sounds auscultated from the body of a patient. Based upon measurements taken of the different sounds, medical practitioners have been able to diagnose diseases and proceed with treatments.

In order to make a precise diagnosis of an ailment based upon auscultated sounds, extensive empirical knowledge of various and diverse forms of auscultated sounds is necessary. Until recently, auscultation was more art than science since making a diagnosis was based mainly upon the trained ear of a caregiver and not based upon objectively measured data from recorded sounds.

With the advent of digital/electronic stethoscopes, auscultated sounds can be recorded in digital form, and computer programs manipulate the data to analyze characteristics of the recording. From this analysis, more precise diagnoses can be made based upon objective criteria and not just upon the trained ear of the attending caregiver.

It is well known to measure auscultated sounds from humans in order to make diagnoses of perceived pathology. However, auscultation for animals such as cattle is used infrequently. There have been very few efforts made to gather data from auscultated sounds for purposes of making conclusions as to the type of disease that may be occurring in a species of animal.

Particularly in a feed yard where it is necessary for cattle to be maintained at an optimum state of health for maximum weight gain to occur, it is critical that sick cattle be identified early for effective treatment and to contribute to biosecurity. The true state of health for cattle can be difficult to measure using traditional techniques such as observation of symptoms to include temperature, posture and visual signs (e.g. nasal discharge, depression, and abdominal fill). In the example of the bovine species, case definitions for BRD traditionally include a minimally effective but objective rectal temperature and a subjective clinical score. Clinical trials indicate that objective lung scores provide stronger correlations than rectal temperatures to ultimate case fatality rates, retreatment rates, and therefore treatment costs. Cattle are visually evaluated when they first arrive at the feed yard, and the surge of adrenalin associated with handling, along with prey defensive mechanisms, can often mask disease symptoms. Stethoscopic evaluation of bovine heart and lung sounds can be used to evaluate the cardio-pulmonary efficiency or potential efficiency of cattle during various stages of arrival processing. However, because of the lack of current data in objectively categorizing animal heart and lung sounds, there is a need for developing an automated system and method that can assist a caregiver in assessing these sounds and making timely diagnoses.

Bovine respiratory disease is complex and is particularly difficult to accurately diagnose in the harsh environments where the animal's health assessment takes place; noisy with uncooperative patients at best requiring server restraint. The thick musculature that surrounds the thorax of cattle, the heavy hide and layers of fat renders the use of a stethoscope difficult to obtain sounds that can be interpreted for purposes of making an accurate diagnosis. Because of the difficulties encountered to effectively gather auscultated sounds from cattle, and a general lack of knowledge in the cattle industry as to how to interpret these sounds, the cattle industry has been slow in developing automated diagnostic processes that can effectively use data generated through auscultation.

Production animals are intentionally metabolically stressed to promote rapid weight gain in the feed yard. Nutrition technology and health management protocols strive to maximize daily weight gain, but weight gain itself can push the physiological limits of production animals beyond their ability to mount a compensatory response to; metabolic challenges, disease, weather environmental, and behavioral stresses. Determining the physiological capacity for stress of each production animal would allow for matching of the animal to an optimal production management strategy protocol. This optimization would enhance the production process causing a higher rate of return by minimizing valuable asset loss due to animal variations in abilities to handle physiological stress. If an animal's compensatory capabilities could be predicted prior to exposing the animal to the stresses inherent in production, then optimal production procedures could be implemented for each animal given its unique physiological profile and thus maximizing each animal's potential and minimizing each animals risks.

Cardiac performance/efficiency is measured by the cardiac output (CO) of an animal and is defined as heart rate (HR) multiplied by the stroke volume (SV) thus this relationship can be expressed as $CO=(HR)(SV)$. The heart rate of an animal will typically increase at times of acute stress (both physical and psychological) due to increased automaticity (and therefore an increased rate) caused by catecholamine release during a sympathetic adrenergic response to stress. For production animals such as beef cattle, processing actions such as experienced in transporting the animals to and sorting the animals within a feed yard can be a series of very stressful events that predictably drive up the heart rates of the animals due to positive chronotropic effects of the sympathetic nervous system.

Respiratory performance/efficiency of an animal is the ability of the pulmonary system to adequately exchange gases allowing for metabolic variations while maintaining optimal functioning of vital organs. Part of the mechanism for handling the variations of metabolic changes is through perfusion matching with ventilation. Ventilation or respiratory drive, can in part be measured by respiratory rate.

When either the cardiac function or respiratory function is impaired, the other system may respond through compensatory mechanisms that attempt to maintain homeostasis for the animal. Maintaining homeostasis becomes more challenging if an animal is placed in stressful environments. Maintaining homeostasis under an impaired condition will consume organ system resources, and the animal may not be able to maintain homeostasis. The compromised state of an animal in this condition causes a reduction in the efficiencies of the animal's metabolic system, which in turn manifest in consequences such as a decreased daily weight gain or observable increases in morbidity.

Therefore, in the case of the bovine, in addition to an acute lung score for lung pathology detection, there is a need to determine which production animals may be prone to not tolerating metabolic stress or may be inefficient in adapting to metabolic stresses that could result in poor performance over time. The poor performance can range from inadequate weight gain to acute morbidity and/or mortality.

While there may be some known methods and systems that account for cardiac performance in determining the health status of animals, there is a further need to provide new ways of determining when animals that are not capable of tolerating metabolic stress so that very early predictions can be made about the performance potential of an animals.

SUMMARY OF THE INVENTION

According to the invention, vital signs of an animal are recorded in a stress inducing situation or environment that would likely elicit an adrenergic sympathetic "flight or fight" reaction. This environment maximizes the likelihood of anomaly detect. The vital signs recorded include the heart and respiration rates. The vital signs are analyzed to determine whether compensatory changes may reflect on the animal's ability to tolerate stresses that some conditions may place on the health of the animal. From the compensatory changes observed, various conclusions can be made regarding better treatments that can be pursued for sick animals and for more accurately predicting outcomes for those animals in terms of whether an animal can reach production standards, or whether the animal may require excessive treatment and costs to reach production standards.

One example of an environment or situation that may elicit adrenergic sympathetic reactions is actions that take place during processing beef cattle at a feed yard upon arrival to the feed yard. In this situation, the animals are typically agitated and therefore show cardio-pulmonary signs of sympathetic adrenergic stress reactions including tachycardia (rapid heart rate) and tachypnea (rapid breathing). In another example, the invention contemplates use of a controlled stress producing event which is known to generate adrenergic responses in animals. The purpose of this controlled stress producing event is to normalize the effects on a group of animals so there is less of a likelihood of random stress responses with the events that could disproportionately influence a selected few animals.

The invention as described in more detailed below is a result of further observations and conclusions regarding cardiac and pulmonary (cardio-pulmonary) subsystems of an animal. These cardio-pulmonary subsystems of an animal can conceptually be described as subsystems that work together to create a synergistic outcome that maintains homeostasis within a given animal. In normal physiology, these subsystems respond to the needs of the animal maintaining a constant relative relationship of efficiencies and performance. That is, in times of high metabolic demands both cardiac and pulmonary systems will increase functional output to accommodate the change in metabolism. This is best observed during physical exercise. If metabolic demands drop to a basal level, then correspondingly so will the level of performance for each component of the cardio-pulmonary system. These high and basal metabolic fluctuations in rates for a normal functioning cardio-pulmonary systems can describe a relatively constant ratio between cardiac output and pulmonary performance. However, if either the cardiac output or pulmonary performance is inefficient, then this relative ratio will be altered especially as the metabolic demands increase or in times of stress both physical and psychological. So it is with this ratio (Cardio-Pulmonary Ratio or CPR) that we can observe relative differences in subsystem efficiencies. These differences can manifest in terms of compensatory changes to the heart rate and breath rate which allow for any deficits in efficiencies to be mitigated. Changes in either the cardiac or pulmonary system efficiencies can occur due to disease (acute and chronic) or congenital defects. The concept of the cardio-pulmonary ratio (CPR) of the present invention is focused on the relative relationship between the heart rate and breath rate and not their absolute values. For example; an animal with a high fever and normal cardio-pulmonary function will have elevations in both heart rate and breath rate thus maintaining the relationship between the two systems in the context of high absolute values on the rates of each subsystem. An animal with impaired organ function in the cardio-pulmonary system will likely need to compensate for the impaired organ's inefficiencies and produce a discordant rate drive in either the cardiac or pulmonary system. The compensation can result in a normal appearing animal but will leave the animal less adaptable functional performance room in the face of stressors such as disease or weight gain or weather and hydration.

According to the invention, an assumption is made that there is generally a linear relationship between heart rate and respiratory rate. Thus the higher the heart rate, the proportionately higher the respiratory rate must be to match ventilation requirements. Anomalies can be detected when the relationship deviates from an expected linear trend. Thus higher heart rates with disproportionately lower respiratory rates or lower heart rates with disproportionately higher respiratory rates may indicate cardio-pulmonary performance abnormalities.

The linear trends can be expressed in terms of data points normalized with values plotted as curves on a graph. Cardio-pulmonary performance abnormalities can therefore be shown as curve deviations that may indicate heightened risks for diseases such as; BRD, acidosis, ketosis, or Brisket disease at lower elevations. These deviations can be numerically quantified and correlated to odds or chances that a particular animal has or will develop the condition or disease. The cardio-pulmonary status of an observed animal can be expressed as a cardio-pulmonary rate ratio profile, and animals can then be sorted by their cardio-pulmonary rate ratio profiles to place the animals in an optimized management program given their capacities or lack thereof to tolerate stress.

Cardiopulmonary data can be obtained using an electronic stethoscope, such as disclosed in the U.S. application Ser. No. 13/442,569 entitled System and Method for Diagnosis of Bovine Diseases Using Auscultation Analysis, this application being incorporated by reference herein in its entirety. One minor change that could be incorporated within the electronic stethoscope disclosed in that US application is that normally, the cardio generated sounds are filtered to therefore amplify and clarify respiratory sounds. However in the present case, the electronic stethoscope is used to obtain simultaneous data on both the respiration rate and heart rate of the observed animal; accordingly, cardio sounds do not require filtering.

The detected anomalies for deviations in the linear relationship between respiration rate and heart rate can be mathematically expressed by first applying a formula to measured heart rates and respiration rates to place the corresponding rates on a normal or bell shaped curve created by sampling a large set of lung sounds. For this invention, 70,000 sounds were used to generate the averages and distributions. This gives relevance to the rates now expressed with a value between 0 and 1 representing their position on the bell shaped curve. The cardio-pulmonary rate ratio is then determined by dividing the final normalized adjusted heart rate value by the final normalized adjusted respiratory value. From the values calculated for each of the sample animals and their heart and respiratory rates, a usage range is established on both curves which indicates the lower and upper bounds of values used in the calculated ratio. This calculated cardio pulmonary rate ratio is then also normalized to a value of 0 to 1 on the bell shaped curve.

The cardio pulmonary rate ratios (CPR) may be expressed as numerical scores, and these scores may be divided into categories that generally characterize the compensatory responses of the animals evaluated. The first category is respiratory compensating (CPR-R) which corresponds to those animals that generally compensate or respond to induced stresses by changes in respiration rates. The second category is cardiac compensating (CPR-C) which corresponds to the animals that the generally compensate or respond to induced stresses by changes in heart rates. A third category is normal or non-compensating (CPR-N), which corresponds to those animals that do not exhibit suspect or out of range responses to induced stresses. A fourth category combines animals from both the respiratory compensating and cardiac compensating groups into one group of compensators as some disease etiologies can induce either a cardiac or respiratory compensating response (CPR-RC). Accordingly, this group represents those animals that have either a respiratory or a cardiac compensating response.

CPR ratio values found at the lower end of the ratio range can be those ratios having a value of 0.15 or less. These ratios indicate higher relative respiration rates therefore indicating respiratory compensation due to disease or other physiological anomalies. Accordingly, this range of values can be categorized as respiratory compensating (CPR-R).

At the highest end of the calculated CPR curve (0.85 or greater), this range of values corresponds to those animals that may have a disproportionately higher heart rate given their respiratory rate. It is possible that these animals are compensating for a low cardiac output (CO) which could impact their ability to tolerate rapid weight gain. Accordingly, this range of values can be categorized as cardiac compensating (CPR-C). Either end of the spectrum of ratios may indicate compromised cardio-pulmonary function and therefore compensating animals that fall within the designated compensating categories are considered suspicious for normal cardio-pulmonary function.

CPR ratio values found between 0.15 and 0.85 can be categorized as normal or non-compensating (CPR-N). Unless other observations are made with animals having CPR ratio values within this range, there is a general presumption that these animals are not symptomatic for any particular ailment or anomaly.

Early detection of cardio-pulmonary compensating animals may enhance overall production and reduce production costs by sorting those animals with significant inefficiencies into better suited production management programs. Using a CPR analysis for companion animals may assist in defining appropriate activities or direct treatments that improve the quality of life for the animal.

The present invention in broad terms provides CPR values for individual animals in which a particular animal's CPR value or score can be placed within a normalized curve of data points for a population of animals within that specie and wherein each animal within the population of animals have respective CPR scores that were measured within the same stressed environment. Since the population has measured data points within the same environmental conditions as a particular animal being evaluated, this increases the likelihood that the conclusions made about the particular animal are accurate predictions regarding the future health of the animal, and its ability to reach production goals, or to otherwise perform according to expected standards.

One other aspect of the invention is that while respiratory rates do expectedly correlate positively and significantly with animal body temperature, computed CPR values or scores are "body temperature neutral" meaning there is no required measured parameter that correlates CPR values with body temperature. Accordingly, the CPR values can provide new information about the health condition of an animal without having to obtain an animal's temperature. Further, the CPR value provides new information about the health condition of an animal without having to obtain separate or additional data on auscultation, whether the auscultation is expressed in terms of a lung score or some other calculated value.

According to another aspect of the invention, the use of the CPR values can be used in conjunction with auscultation data in order to identify non-BRD pathology by fining animals without presumptive BRD from auscultation data, but who are categorized as respiratory compensating (CPR-R). As further discussed in the detailed description, the non-BRD pathology analysis is yet another feature of the invention that can be derived from CPR values. From this analysis, predictive information can be obtained regarding morbidity and mortality outcomes. One type of auscultation analysis that is particularly useful with CPR values of the present invention is a lung scoring method disclosed in the above mentioned U.S. application Ser. No. 13/442,569 hereby incorporated by reference in its entirety. According to the invention disclosed in this US application, a system and method are described for diagnosis of animal respiratory diseases using auscultation techniques. Animal lung sounds are recorded and digitized. Lung sounds are obtained by an electronic digital stethoscope or a wireless audio digital recording unit. The sounds are stored as digital data, and one or more algorithms are applied to the data for producing an output to the user indicative of the health of the animal. Acoustic characteristics of the sound are compared with baseline data in the algorithms. One embodiment includes a digital stethoscope with an integral display. Another embodiment provides a system for gathering information about an animal to include not only auscultation data, but also information from other field devices such as temperature probes or weigh scales. The combined information can be analyzed by system software to generate detailed information to a user to include a diagnosis and recommended treatment options. According to a method disclosed in this U.S. application Ser. No. 13/442,569, it includes a method for diagnosing animal diseases using auscultation analysis, said method comprising: (i) recording auscultated sounds from an animal by an electronic digital stethoscope and converting the sounds to digital data; (ii) converting the digital data to data in a frequency domain; (iii) separating data in the frequency domain into predetermined desired groups of amplitudes and frequencies forming converted data; (iv) applying an algorithm to the converted data to generate at least one of a value or visual indication that corresponds to a state of health of the animal; (iv) providing an integral display on the digital stethoscope; and (v) generating an output on the display for observation by a user indicating to the user a status of health of the animal.

According to another method disclosed in this U.S. application Ser. No. 13/442,569, it includes a system for gathering information regarding an animal and using the information for determining a state of health of the animal, said system comprising: (i) a wireless electronic digital stethoscope for recording auscultated lung sounds obtained from the animal in the form of digital sound data; (ii) a processor for processing the digital sound data; (iii) computer coded instructions for manipulating the digital sound data through incorporation of at least one algorithm used to calculate a value, said algorithm utilizing selected frequencies of the auscultated sounds, said algorithm generating a first set of data; (iii) said first set of data recorded in a database of said processor and said first set of data reflective of a diagnosis that corresponds to the values obtained from the algorithm; (iv) a user display incorporated on the digital stethoscope for displaying information reflective of a state of health of the animal corresponding to the diagnosis and to additional health information; (v) at least one field device wirelessly communicating with the stethoscope, said field device including at least one of a weigh scale, an RFID reader, a diagnostic device, and a temperature probe; and (vi) a second set of data obtained from the field device as prompted by a polling command from the stethoscope, wherein the second set of data corresponds to additional data obtained from the field device for the animal, and the first and second data sets collectively are provided to the user display corresponding to the additional health information. With respect to use of the stethoscope, the device may include a health status indicator in the form of a plurality of health indicator lights. These indicator lights may represent a lung score, or may represent some other indication as to the health of the animal. In one embodiment of the stethoscope, they may be numbered, for example, from 1-5. The illumination of one of the lights or a group of lights indicates a lung score or some other health status for the animal. For example, light number one (1), if illuminated, could indicate a normal condition for the animal. Light number two (2), if illuminated, could indicate a mild, acute condition. Light number three (3), if illuminated, could indicate a moderate acute condition. Light number four (4), if illuminated, could indicate a severe acute condition, and light number five (5), if illuminated, could indicate a chronic condition. As further discussed in the detailed description, the non-BRD pathology analysis is yet another feature of the invention that can be derived from CPR values in conjunction with the auscultation data.

According to yet another feature of the invention, use of the CPR values with auscultation data or information can be provided to generate improved risk stratification of BRD cases with categorized lung score groups from the auscultation data. For example, use of the CPR values can produce predictive information for morbidity and mortality outcomes based on lung score groups or categories.

According to yet another aspect of the invention, the use of CPR values can be used to detect abnormalities in the lungs of an animal, such as lung lesions that impact cardiovascular performance and may therefore indicate a long-term decrease in production performance of the animal. One particularly advantageous aspect of the invention is that a simple analysis of only respiratory rate and heart rate will not allow a reasonable conclusion to be made regarding lung abnormalities such as lung lesions, since there is no identifiable pattern of association between absolute heart and breath rates. Through CPR, which transforms the absolute rate values into clinically meaningful information, an association between the animal's vital sign rates and lung lesions is apparent and predictable.

According to yet another aspect of the invention, the use of CPR values can be used to predict performance metrics or performance measurements, such as the average daily weight gain of an animal in a feedlot. CPR values may be used in conjunction with other biometrics to drive real-time best choice antibiotic and dietary treatment programs at point of care.

According to yet another aspect of the invention, it can be used for a clinical decision making algorithm to drive treatment options based on predicted outcomes of on-going analysis using digitized bio-metric data like CPR values of the present invention. CPR values may be used as vital indicators of the overall health status of an animal and can contribute to diagnostic information by transferring real-time data to a repository cloud database for modeling treatment efficacies. From the modeling, probable outcomes for animal performance can be created including economic impact assessments that direct optimal disease management strategies such as best choice of antibiotic and dietary changes. CPR values combined with a lung scoring algorithm and other animal health data such as health history, body temperature, previous drug treatments, weight changes, weather reports, and morbidity and mortality rates can allow the creation of combinatorial optimization treatment suggestions to animal caregivers. A system of health data capture according to this aspect of the invention can drive analytical models that deliver evidence based medicine and adjust treatment recommendations from real-time feedback-loop information. Capturing physiological information on animals and sending it immediately to a cloud server for insertion into a machine learning module that communicates immediately back to the point of care decision for treatment may favorably shift morbidity and mortality trajectories, and at the same time minimize costs. This method of real-time feedback regarding preferred treatments for individual animals may be particularly advantageous with respect to use of antibiotics selected for treatment. Further, this method may enhance clinical decision making of veterinarians on a day-to-day basis as they will have information immediacy and clinical relevance not available from prior systems or methods. The use of CPR values in this method is ideal because CPR values incorporate diagnostic information that is applicable to the health of the whole animal and across multiple disease spectrums.

Considering the above features and attributes of the invention, the invention can be further defined as a method for assessing animals considering physiological responses to stress, comprising: (a) exposing an animal to a controlled environment known to induce sympathetic adrenergic stress reactions; (b) recording heart and respiration rates of an animal during said reactions; (c) determining a cardiopulmonary rate ratio for the animal expressed as the heart rate divided by the respiration rate; (d) determining a range of ratios for a plurality of animals within an observed population of animals; (e) determining a group of first values for ratios indicating respiratory compensating responses (CPR-R); (f) determining a group of second values for ratios indicating cardiac compensating responses (CPR-C); (g) determining a group of third values for ratios indicating normal compensating responses (CPR-N); (h) determining a likelihood an animal will develop a disease taking into account said ratios within said first, second, or third groups of values; and (i) providing treatment to the animal corresponding to the likelihood the animal will develop the disease. Other aspects of the invention can be defined according to this method for assessing animals to further include any one of or any combination of: (a) determining a weight for the animal and then determining a likelihood an animal will develop a disease taking into the weight of the animal (b) wherein the cardiopulmonary rate ratio is determined by dividing a final normalized adjusted heart rate value by a final normalized adjusted respiratory value (c) the cardiopulmonary rate ratio is determined by dividing a final normalized adjusted heart rate value by a final normalized adjusted respiratory value (d) conducting an auscultation analysis for each animal and providing treatment to the animal further considering results of said auscultation analysis (e) wherein the auscultation analysis further includes designation of a lung score for the results corresponding to the analysis and (f) said treatment includes at least one of administration of an antibiotic, administration of a selected nutrition program, or combinations thereof.

Further considering the above features and attributes of the invention, the invention can be further defined as a method of establishing a CPR value for at least one animal within a population of similarly situated animals in a selected environment considering physiological responses to stress therein and using the CPR value for treatment, said method comprising:

convert empirical distributions of breath and heart rates of an animal into a standard normal distribution curve by: (i) recording breath and heart rates of a large sample of similar animals; similar in breed, weight and health status: (ii) for breath rates, transform the empirical distribution into a standard normal distribution for use to determine an animal's breath rate location on a cumulative normal density curve giving a value between 0 and 1; (iii) for heart rates; transform the empirical distribution into a standard normal distribution for use to determine an animal's heart rate location on a cumulative normal density curve giving a value between 0 and 1;

develop CPR norms by: (i) calculating a raw CPR value from a value of a corresponding normalized heart rate divided by a value of the breath rate and applied only to animals with values greater than 0 on both normalized breath and normalized heart rates; and (ii) taking the raw CPR values calculated and transform the empirical distribution of the raw CPR values into a standard normal distribution for use to determine an animal's CPR value as a location on a cumulative normal density curve giving a value between 0 and 1;

generate CPR norms by: (i) capture an animal's breath and heart rate; (ii) calculate a normalized breath rate cumulative density value (0 to 1) using the transformation determined; (iii) calculate a normalized heart rate cumulative density value (0 to 1) using the transformation determined; (iv) calculate a ratio of the heart rate normalized value to a breath rate normalized value; (v) calculate a normalized CPR value cumulative density value (0 to 1) using the transformation equation determined; and (vi) assign a CPR category from a value using category determiners as follows:

If equal to or less than 0.15, then animal is categorized as a respiratory compensator (CPR-R);

If equal to or greater than 0.85, then animal is categorized as a cardiac compensator (CPR-C); and If greater than 0.15 and less than 0.85, then animal is categorized as a non-compensator/normal (CPR-N).

(d) reviewing determined CPR categories for animals selected for treatment; and (e) conducting treatment for the selected animals.

Yet further considering the above features and attributes of the invention, the invention can be further defined as a method for assessing animals considering physiological responses to stress, comprising: exposing an animal to a controlled environment known to induce sympathetic adrenergic stress reactions; recording heart and respiration rates of an animal during said reactions; determining a cardiopulmonary rate ratio for the animal expressed as the heart rate divided by the respiration rate; determining a range of ratios for a plurality of animals within an observed population of animals; and providing treatment to the animal corresponding to a likelihood the animal will develop the disease by analyzing the cardiopulmonary rate ratio. Other aspects of the invention can be defined according to this method for assessing animals to further include any one of or any combination of: determining a group of first values for ratios indicating respiratory compensating responses (CPR-R); determining a group of second values for ratios indicating cardiac compensating responses (CPR-C); determining a group of third values for ratios indicating normal compensating responses (CPR-N); and determining a likelihood an animal will develop a disease taking into account said ratios within said first, second, or third groups of values.

The above features of the inventions and others will become more apparent from a review of the following detailed description, along with the attached figures.

DETAILED DESCRIPTION

Figure 1:
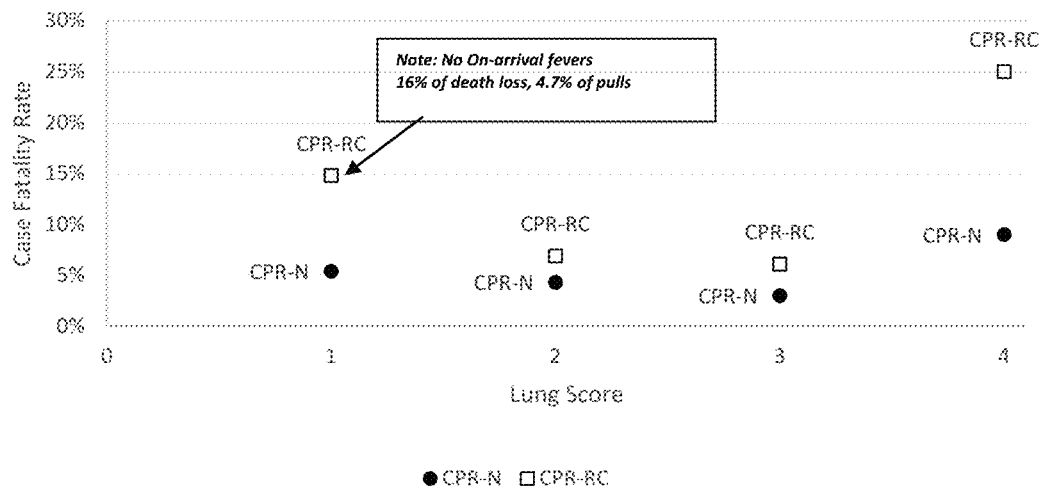
FIG. 1 is a visual depiction of example data points on a graph which illustrate how CPR values of the present invention can be used with auscultation data to identify non-BRD pathology.

The creation of CPR values for the present invention is optimized if large samples of data are used to establish norms that indicate true high and low values of vital signs within a species for a given environment. CPR values can be determined for any species of animal in which preferably large samples of data are used to establish norms, and in which a preferred protocol for obtaining respiration and cardiac rates are to be taken from the same type of stress-induced environment for each animal. More specifically, the CPR values are more reliable when each animal of the population is exposed to the same or similar stress induced environment.

Set forth below is an example method/protocol of the invention for establishing a CPR formula or mathematical expression for a species, such as a bovine species:

Convert empirical distribution of breath and heart rates of a given species and breed into standard normal distribution curves $\sim N(\mu=0, \sigma=1)$.

Determine or capture the breath and heart rates of a large sample of similar animals; similar in breed, weight and health status. Preferably obtain captured data for many animals.

For breath rates; using the data in step 1a, transform the empirical distribution into a standard normal distribution $\sim N(\mu=0, \sigma=1)$ which can be used to determine an animal's breath rate location on a cumulative normal density curve giving a value between 0 and 1.

For heart rates; using the data in step 1a, transform the empirical distribution into a standard normal distribution $\sim N(\mu=0, \sigma=1)$ which can be used to determine an animal's heart rate location on a cumulative normal density curve giving a value between 0 and 1.

Develop CPR Norms.

For each animal in the sample; a raw CPR value is calculated from the value of their normalized heart rate (step 1c) divided by the value of the breath rate (step 1b). This is applied only to those animals with values greater than zero on both the normalized breath and normalized heart rates.

Taking the ratio values created in step 2a, transform the empirical distribution of the raw ratio values into a standard normal distribution $\sim N(\mu=0, \sigma=1)$ which can be used to determine an animal's CPR score or value as a location on a cumulative normal density curve giving a value between 0 and 1.

Utilization of CPR Norms

Capture an animal's breath and heart rate.

Calculate the normalized breath rate cumulative density value (0 to 1) using the transformation equation determined in step 1b.

Calculate the normalized heart rate cumulative density value (0 to 1) using the transformation equation determined in step 1c.

Calculate the ratio of the heart rate normalized value (step 3c) to the breath rate normalized value (step 3b).

Calculate the normalized CPR value cumulative density value (0 to 1) using the transformation equation determined in step 2b.

Assign the CPR category from value in step 3e using the following determination cut-off points.

If equal to or less than 0.15, then animal is a categorized as a respiratory compensator (CPR-R).

If equal to or greater than 0.85, then animal is categorized as a cardiac compensator (CPR-C).

If greater than 0.15 and less than 0.85, then animal is categorized as a non-compensator/normal (CPR-N).

Based upon the foregoing explanation, one example formula to describe a CPR score or value may be expressed as follows:

$$CPR = e^{\wedge}(-(-10+(ASINH(((e^{\wedge}(-(0.6+1\cdot{}^*LN(((LN(HeartRate)-4))/((6-LN(HeartRate))))))^{\wedge}2/2)/e^{\wedge}(-(0.3+LN(((BreathRate-3))/((100-BreathRate))))^{\wedge}2/2)+0.03))/0.00001)))^{\wedge}2/2)\sqrt{2\pi}$$

Referring now to the Figures, FIG. 1 is a visual depiction of data points on a graph which illustrate how CPR values of the present invention can be used with auscultation data to identify non-BRD pathology. More specifically, FIG. 1 shows example data concerning classification of CPR scores or values for a group of observed animals. The background information on the animals is that they arrived to a location, such as a feedlot, and each animal in the group was previously treated with antibiotics. The number of animals in the population/observed group is 1,069 animals. Each of the animals were evaluated in terms of obtaining auscultation data, such as a corresponding lung score as disclosed in the above mentioned U.S. application Ser. No. 13/442,569. Each of the animals were also evaluated by generating corresponding CPR scores, and specific data points shown in the graph correspond to groups of animals within the population that had the corresponding CPR scores. As further shown in the graph, the two general categories of CPR evaluations recorded include CPR-N and CPR-C. On the right side of the graph along a lung score of 4, as expected, there was a fairly high case fatality rate for those animals which had a high lung score and which were determined as having respiratory compensating or cardiac compensating CPR scores. However, the graph also shows a high case fatality rate for one group of animals on the left side of the graph along a lung score of 1. Although these animals had presumably healthy respiratory systems because of the low lung score, there was still a high fatality rate that cannot be explained by just an evaluation of auscultation data. This elevated case fatality rate is only observable as a function of the determination of CPR scores for this group of animals, and it can therefore be deduced that that relatively high fatality rate was due to non-BRD pathology. These animals may also have been observed as not responding to antibiotic use; however, a determination of potential other diseases is simply not possible with auscultation analysis. Therefore, one proposed or prudent treatment that could take place for this group of animals is to withdraw the animals from any antibiotics, and to memorize the animal from other conditions which may contribute to something other than BRD, such as a metabolic disorder. In summary, FIG. 1 is therefore intended to illustrate that although an animal may have a favorable lung score, increased fatality rates for these types of animals can be difficult to predict unless there's some type of other measurement parameter which may provide a caregiver, a more thorough and comprehensive diagnostic analysis of the state of health of the animal.

Figure 2:
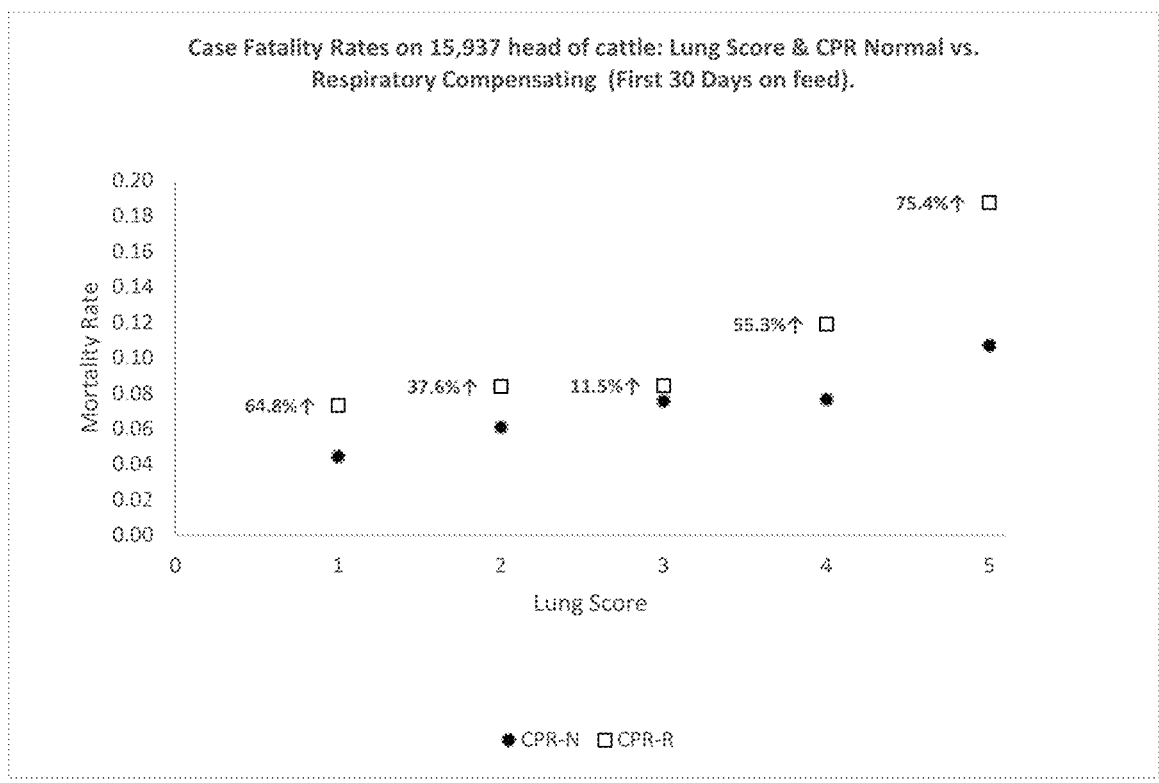
FIG. 2 is another depiction of example data points on a graph which illustrate how CPR values of the present invention can be used with auscultation data to identify risk stratification of BRD as classified according to lung score groups.

Referring to FIG. 2, another graph shows how CPR values of the present invention can be used with auscultation data to identify risk stratification of BRD as classified according to lung score groups. As reflected in this figure, the data points correspond to a study of groups of animals characterized as either CPR-N or CPR-R, and the population or sample was 15,937 head of cattle. There are few conclusions that can be drawn from a review of these recorded data points. First, the graph shows that there was an increased fatality rate for animals across all ranges of the lung scores when comparing animals classified as CPR-R versus CPR-N. In other words, the fatality rate increased for animals having a respiratory compensating response as opposed to those animals that did not have a respiratory compensating response, and this increase occurred even with animals having low lung scores, that is, those animals in which presumptive diagnoses could be made regarding BRD by review of only auscultation data. As shown in the graph, for observed animals having a lung score of 1, there was a 64.8% increase in mortality rates when comparing CPR-R versus CPR-N; for observed animals having a lung score of 2, there was a 37.6% increase in mortality rates when comparing CPR-R versus CPR-N; for observed animals having a lung score of 3, there was a 11.5% increase in mortality rates when comparing CPR-R versus CPR-N; for observed animals having a lung score of 4, there was a 55.5% increase in mortality rates when comparing CPR-R versus CPR-N; and for observed animals having a lung score of 5, there was a 75.4% increase in mortality rates when comparing CPR-R versus CPR-N. Another general conclusion that can be drawn from the data shown in this graph is that some animals classified in one lung score with CPR-R should be considered for a different treatment protocol because the increased mortality rate places or qualifies him for consideration for treatment in a different lung score/category. More specifically, the animals categorized as CPR-R with a lung score of 2 had a slightly higher mortality rate than those animals classified as CPR-N and a lung score of 3. Therefore, a caregiver may wish to alter the treatment protocol for these animals to correspond to the treatment being given for animals having a lung score of 3.

Figure 3:
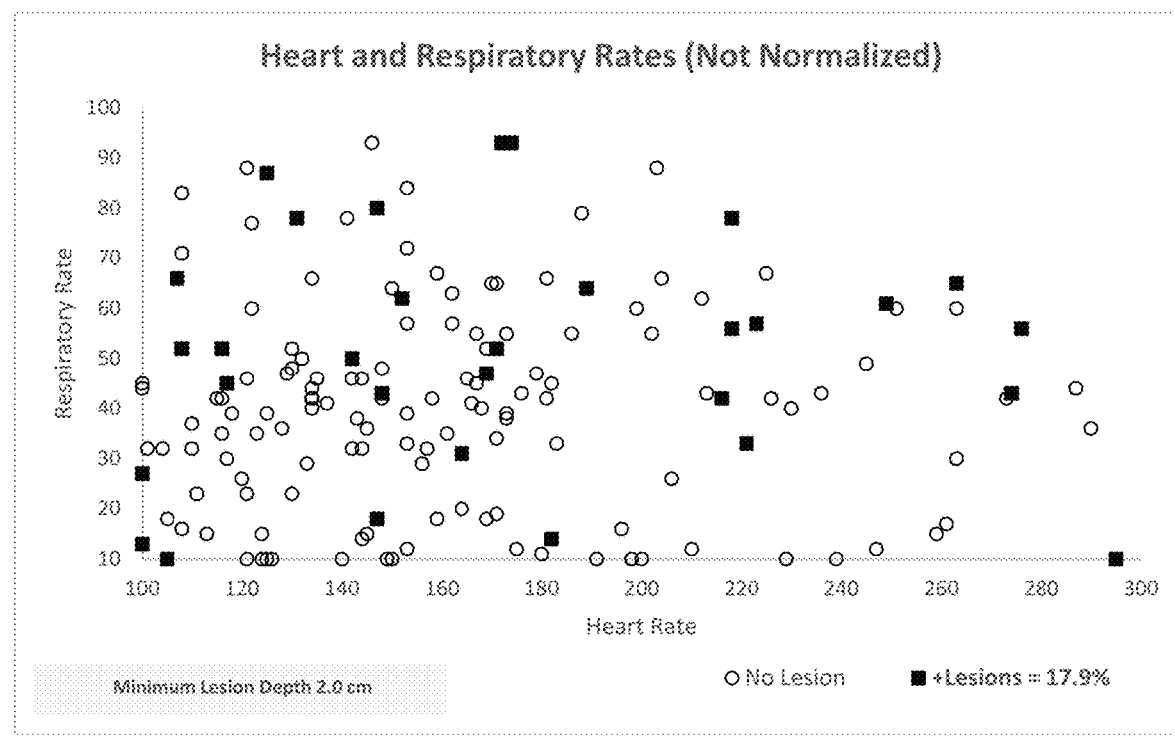
FIG. 3 is a visual depiction of example data points showing lung lesions identified through ultransonography plotting by absolute values of heart and respiratory rates, and more particularly illustrating why lung ailments such as lung lesions cannot be identified simply by recording such data.

Referring to FIG. 3, this graph provides a visual depiction of data points which illustrates plotting of heart and respiratory rates, and more particularly illustrates why lung ailments such as lung lesions cannot be identified simply by evaluating heart and respiratory rates. More specifically, FIG. 3 illustrates heart and respiratory rate data for a group of animals that were studied to detect the presence of lung lesions. The presence of lung lesions negatively impacts cardiovascular performance and typically corresponds to long-term decreases in production performance. The study included 210 cow calves under 150 pounds, and the animals were analyzed to obtain both lung scores and CPR scores. The presence of lung lesions in the animals were verified by conducting ultrasounds giving CPR a diagnostic sensitivity for lung lesions of 0.82 at a peripheral lung depth of 2 cm or more. The animals with lung lesions as compared to those without lung lesions were indistinguishable in terms of identifiable differences in heart or respiration rates. In other words, by review of only heart and respiratory rates, no conclusions could be made as to differences between the animals. Therefore, it is apparent that a traditional auscultation analysis could not assist in easily distinguishing animals for purposes of detecting lung lesions.

Figure 4:
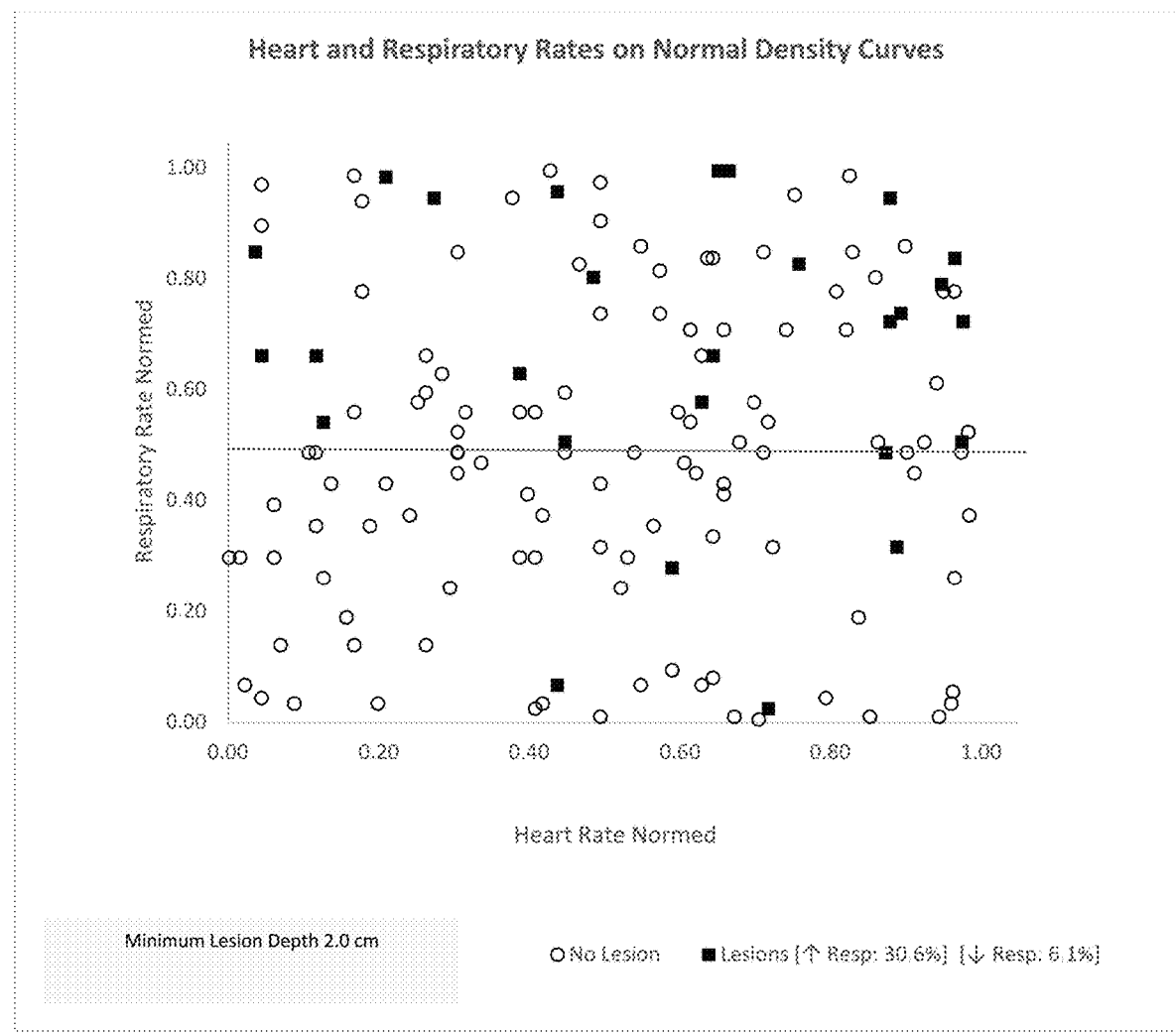
FIG. 4 is another visual depiction of example data points of lung lesions identified through ultransonography which illustrates plotting of heart and respiratory rates, but in which the rates for each axis are normalized to a bell-shaped curve, in which normalization as a component of CPR values of the present invention assist to better separate suspect animals in terms of those having lung abnormalities such as lung lesions and those without such abnormalities.

Referring to FIG. 4, another visual depiction of data points is shown on a graph illustrating plotting of heart and respiratory rates; however, respiratory rates are normalized to a bell-shaped curve, and normalization of the respiratory rates provides an improved indication as to how to distinguish between animals that may have lung lesions. In summary, FIG. 4 illustrates that normalizing the data for the breath rates produces a bell-shaped curve which can be used as more useful information regarding the impact of lung lesions because it can be seen that the lung lesions are much more prevalent in the top 50% of the bell curve as compared to the bottom 50% area. By normalizing the absolute rates, meaningful relationships can be defined between breath rate values beyond their absolute differences. That is; a breath rate difference between 65/min and 55/min is 10/min but the same difference between, for example, 95/min and 85/min is a much rarer occurrence as 95/min is at the tail end of the upper distribution and can be considered almost a statistical outlier. In summary, respiratory rates above a value of 0.50 show much greater density in terms of the number of animals who were detected having lung lesions according to the results of the verifying ultrasound procedures. Normalization is a component of determining CPR values of the present invention and therefore, normalization in this figure indicates that by placing relative frequencies of breath rate occurrences, interpretation of the information is fundamentally changed by adding a new dimension to the data.

Figure 5:
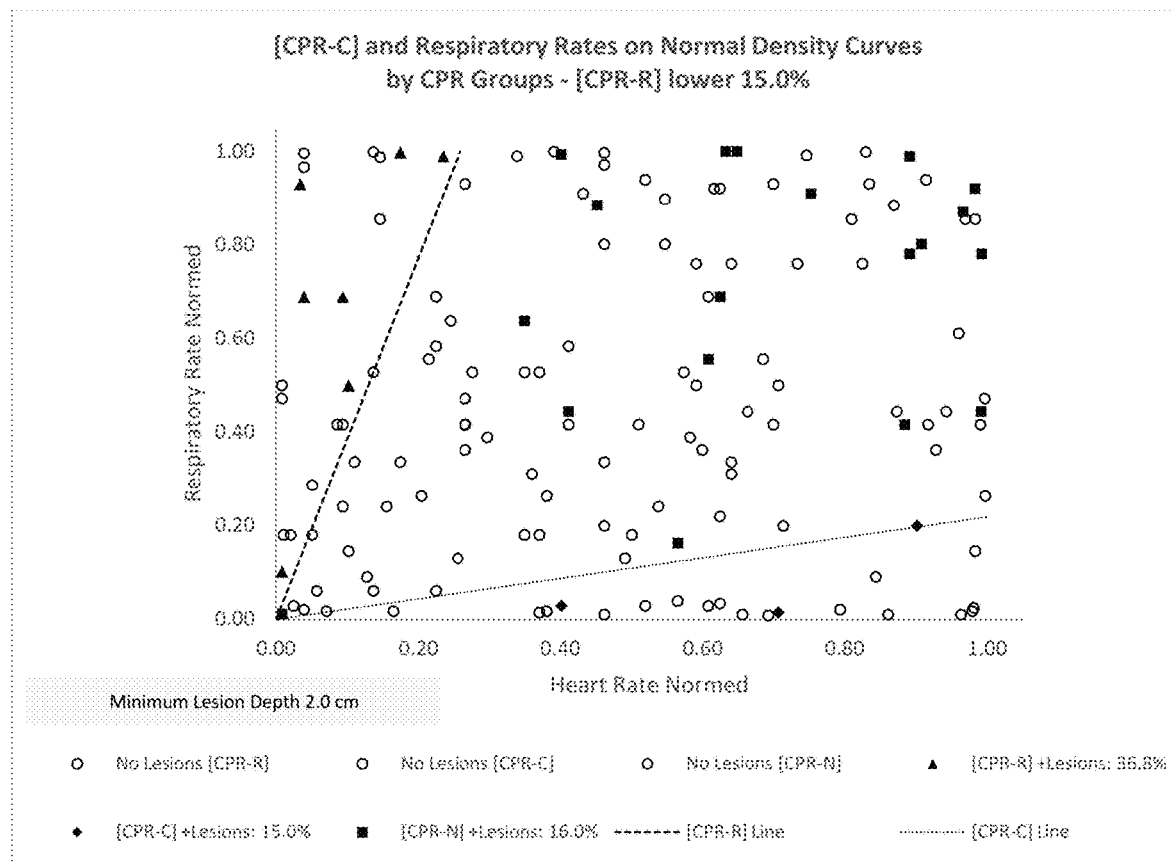
FIG. 5 is yet another visual depiction of example data points of lung lesions identified by ultrasonography which illustrates plotting of heart and respiratory rates according to FIG. 4, with further information added to the graph including separation of the graph into zones corresponding to CPR-R, CPR-N, and CPR-C categories, and the relative abundance (more than twice the rate) of lung lesions in the CPR-R zone compared to the zones for CPR-N and CPR-C.

Referring to FIG. 5, this is yet another visual depiction of data points on a graph which illustrates plotting of heart and respiratory rates according to FIG. 4, with further information added to the graph including separation of the graph into zones corresponding to CPR-R, CPR-N, and CPR-C categories. More specifically, FIG. 5 shows a distribution of minimum lesion depths (2.0 cm) as measured by the confirmatory ultrasounds in which a separation of the graph into the zones provides valuable information regarding those animals that should be targeted for treatment. The dotted line extending from the origin in an upwards manner to approximately 0.20 on the horizontal axis separates data points for those animals classified as CPR-R and CPR-N. The data points for the group of animals to the left of this line are classified as CPR-R, while the data points for the group of animals to the right of this line are classified as CPR-N. The dotted line extending from the origin in a more flat manner and terminating near 1.0 on the horizontal axis separates data points for the animals classified as CPR-N and CPR-C. The data points for the group of animals above and to the left of this line are the animals classified as CPR-N, while the data points for the group of animals below and to the right of this line are the animals classified as CPR-C. One general conclusion that can be made from the use of CPR data in this graph is a prediction of lung lesions known to be associated with lower performance and higher morbidity, and this group of animals correspond to those classified in CPR-R. As shown, the animals classified in this group have more than twice the rate of lung lesions than the other two classified groups of animals. Accordingly, these animals could be selectively treated on arrival to minimize infection spread and minimize re-infection rates. Use of this treatment approach supports best treatment practices to include good antibiotic stewardship and judicious use only for those animals with a diagnosis. Other treatment approaches may be adopted considering other diseases that can be diagnosed early by classification of animals from corresponding CPR categories.

Figure 6:
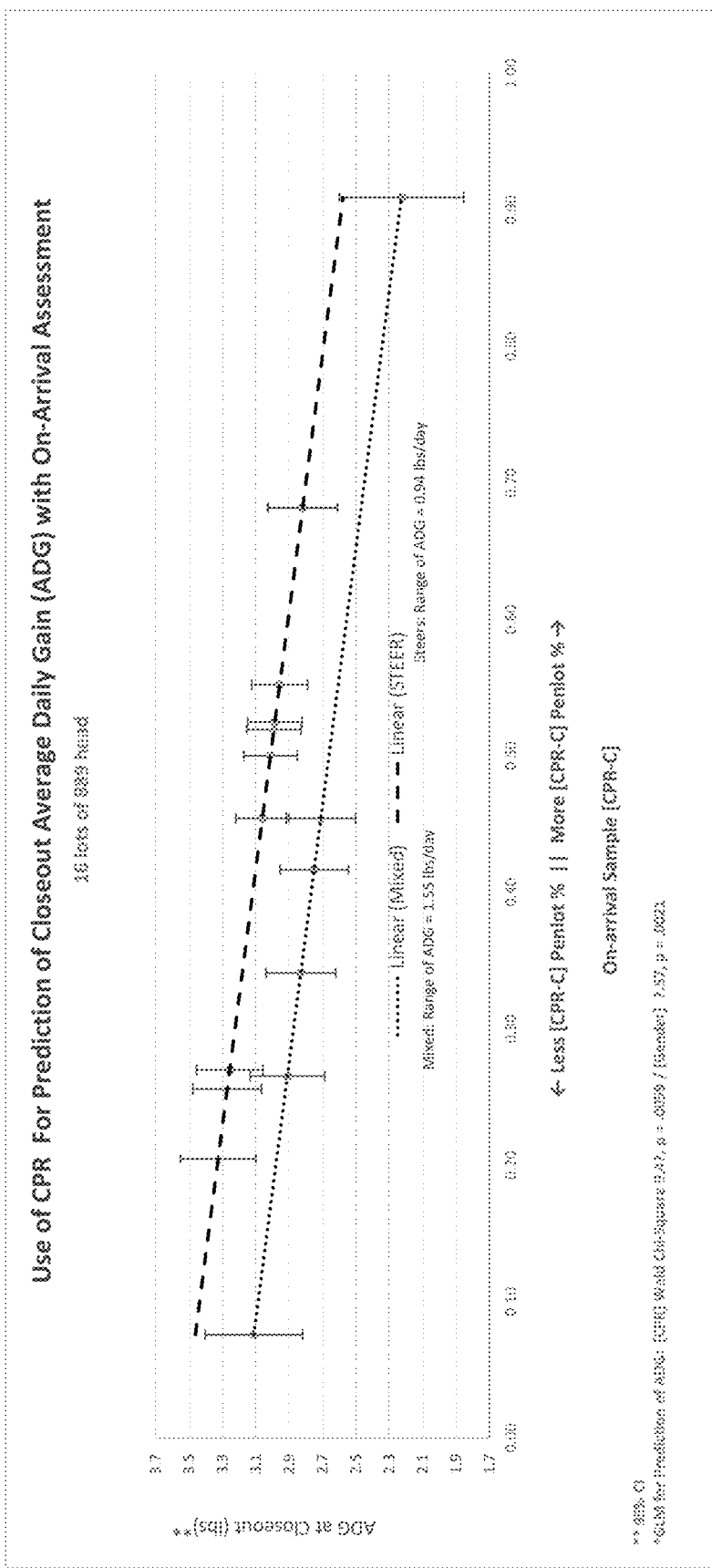
FIG. 6 is another visual depiction of example data points on a graph that illustrates how knowing the percentage of CPR-C categorized animals upon arrival to a location such as a feed yard can provide a more accurate prediction as to performance of animals group within a pen within the feed yard.

FIG. 6 is another graph that illustrates how knowing the percentage of CPR-C categorized animals upon arrival to a location such as a feed yard can provide a more accurate prediction as to performance of animals group within a pen within the feed yard. More specifically, FIG. 6 illustrates that CPR is capable of predicting closeout average daily gain (ADG) by evaluating, for example, a pen lot considering animals characterized as CPR-C. This figure shows to groups of animals, namely, steers and mixed. The vertical axis shows average daily gain at closeout, and the effect of more pronounced cardiac compensating response animals which have a lower average daily gain as compared to those animals which have less pronounced cardiac compensating responses. This figure also shows the difference between steers and mixed, and the overall increased ability for steers to gain weight as compared to mixed animals across a large range of CPR-C values. From an economic standpoint, the linear relationships that can be seen in the graph for both steers and mixed in terms of average daily gain, one may more accurately predict when groups of animals may actually attain desired weight gain goals. Therefore, a more accurate prediction in terms of closeout dates can provide numerous advantages.

It should be understood that the method of the invention can be executed within a data processing system in which the mathematical calculations conducted for the CPA scores and other mathematical calculations relating to auscultation data are manipulated, stored, and made available to a user in various user interface displays. For storage and calculation of data, this can be achieved on a data processing network or within respective standalone data computer systems, depending upon how a user may wish to use and secure the data. It is further contemplated that functionality associated with displaying the results of CPA scores and corresponding auscultation data can be presented to a user on conventional user interface displays, such as screen displays on personal computers, screen displays on mobile devices, and others. FIGS. 1-6 represent exemplary graphs that may be used as displays for data to a user to evaluate and compare groups of animals according to various observed characteristics, to include not only CPR and auscultation data, but any other measured parameters such as animal weight, days on feed, days on antibiotic, and others.

What is claimed is:

1. A method for assessing animals considering physiological responses to stress, comprising:
    exposing an animal to a controlled environment known to induce sympathetic adrenergic stress reactions;
    recording heart and respiration rates of the animal during said reactions;
    determining a cardiopulmonary rate ratio for the animal expressed as the heart rate divided by the respiration rate;
    determining a range of cardiopulmonary rate ratios for a plurality of animals within an observed population of animals;
    determining a plurality of values for corresponding cardiopulmonary rate ratios indicating respiratory responses
expressed as cardiopulmonary rate ratio values, wherein the cardiopulmonary rate ratio of the animal is categorized within one of a compensating response (CPR-R), a cardiac compensating response (CPR-C), or a normal compensating response (CPR-N);
    determining a likelihood the animal will develop a disease taking into account said cardiopulmonary rate ratios of values; and
    providing treatment to the animal corresponding to the likelihood the animal will develop the disease.

2. The method, as claimed in claim 1, further including:
determining a weight for the animal; and
determining a likelihood the animal will develop a disease taking into account the weight of the animal.

3. The method, according to claim 1, wherein:
said cardiopulmonary rate ratio is determined by dividing a final normalized adjusted heart rate value by a final normalized adjusted respiratory value.

4. The method, according to claim 1, further including:
conducting an auscultation analysis for the animal; and
providing further treatment to the animal considering results of said auscultation analysis.

5. The method, according to claim 4, wherein:
said auscultation analysis further includes designation of a lung score for the results corresponding to the analysis.

6. The method, according to claim 1, wherein:
said treatment includes at least one of administration of an antibiotic, administration of a selected nutrition program, or combinations thereof.

7. A method of establishing a cardio-pulmonary ratio (CPR) value for at least one animal within a population of similarly situated animals in a selected environment considering physiological responses to stress therein and using the CPR value for treatment, said method comprising:
    (a) convert distributions of breath and heart rates of an animal into a distribution curve;
    (b) generate CPR norms by:
        (i) capturing the animal's breath and heart rate;
        (ii) calculating a normalized breath rate cumulative density value using determined transformations;
        (iii) calculating a normalized heart rate cumulative density value using a transformation determined;
        (iv) calculating a ratio of the heart rate normalized value to a breath rate normalized value;
        (v) calculating a normalized CPR value cumulative density value using the transformation equation determined; and
        (vi) assigning a CPR category from a value using category determiners as follows:
            If equal to or less than a first numerical value, then the animal is categorized as a respiratory compensator (CPR-R);
            If equal to or greater than a second numerical value, then the animal is categorized as a cardiac compensator (CPR-C); and
            If greater than a third numerical value, then the animal is categorized as a non-compensator/normal (CPR-N),
    (c) reviewing determined CPR categories for the animal selected for treatment; and
    (d) conducting treatment for the selected animal based on the CPR-R, CPR-C and CPR-N values.

8. The method, according to claim 7, further including:
conducting an auscultation analysis for each animal; and
providing further treatment to the animal considering results of said auscultation analysis.

9. The method, according to claim 8, wherein:
said auscultation analysis further includes designation of a lung score for the results corresponding to the analysis.

10. The method, according to claim 7, wherein:
said treatment includes at least one of administration of an antibiotic, administration of a selected nutrition program, or combinations thereof.

11. The method, according to claim 7, wherein:
said CPR norms are developed by:
    (i) calculating a raw CPR value from a value of a corresponding normalized heart rate divided by a value of the breath rate and applied only to animals with values greater than 0 on both normalized breath and normalized heart rates; and (ii) taking the raw CPR values calculated and transform the empirical distribution of the raw CPR values into a standard normal distribution for use to determine an animal's CPR value as a location on a cumulative normal density curve giving a value between 0 and 1.

12. The method, according to claim 7, wherein:

said standard normal distribution curve is determined by:

(i) recording breath and heart rates of a large sample of similar animals that are similar in breed, weight and health status;

(ii) for breath rates, transform the empirical distribution into a standard normal distribution for use to determine the animals' breath rate location on a cumulative normal density curve giving a value between 0 and 1; and (iii) for heart rates, transform the empirical distribution into a standard normal distribution for use to determine the animals' heart rate location on a cumulative normal density curve giving a value between 0 and 1.

13. A method for assessing animals considering physiological responses to stress, comprising:

exposing animals to a controlled environment known to induce sympathetic adrenergic stress reactions;

recording heart and respiration rates of the animals during said reactions;

determining cardiopulmonary rate ratios for the animals expressed as the heart rate divided by the respiration rate;

determining a range of ratios for a plurality of animals within an observed population of animals, said range of ratios including groups of values for respiratory compensating responses (CPR-R), cardiac compensating responses (CPR-C), and normal compensating responses (CPR-N);

providing treatment to the animals corresponding to a likelihood the animals will develop a disease by analyzing the cardiopulmonary rate ratios;

conducting an auscultation analysis for each animal; and providing treatment to the animals further considering results of said auscultation analyses.

14. The method, according to claim 13, further including:

determining a group of first values for ratios indicating the respiratory compensating responses (CPR-R);

determining a group of second values for ratios indicating the cardiac compensating responses (CPR-C);

determining a group of third values for ratios indicating the normal compensating responses (CPR-N); and determining likelihoods animals will develop a disease taking into account said ratios within said first, second, or third groups of values.

* * * * *

UNITED STATES PATENT AND TRADEMARK OFFICE
CERTIFICATE OF CORRECTION

PATENT NO. : 12,193,837 B2
APPLICATION NO. : 18/147564
DATED : January 14, 2025
INVENTOR(S) : Kurt Brattain It is certified that error appears in the above-identified patent and that said Letters Patent is hereby corrected as shown below:

On the Title Page

Item (63) Related U.S. Application Data should read:
Continuation of application No. 16/752,278, filed on Jan. 24, 2020, now Pat. No. 11,642,079, which is a continuation of application No. 15/307,141, filed on Oct. 27, 2016, now Pat. No. 10,575,776, which is a National Stage Entry of PCT/US2015/028373, filed on Apr. 29, 2015.

Signed and Sealed this
First Day of April, 2025

Coke Morgan Stewart
*Acting Director of the United States Patent and Trademark Office*